US005599314A

United States Patent [19]
Neill

[11] Patent Number: 5,599,314
[45] Date of Patent: Feb. 4, 1997

[54] SYRINGE WITH INCREMENTALLY ACTUATED PLUNGER

[75] Inventor: Peter A. Neill, Stowmarket, Great Britain

[73] Assignee: Hypoguard (UK) Limited, Great Britain

[21] Appl. No.: 403,892

[22] PCT Filed: Sep. 20, 1993

[86] PCT No.: PCT/GB93/01978

§ 371 Date: Apr. 26, 1995

§ 102(e) Date: Apr. 26, 1995

[87] PCT Pub. No.: WO94/06494

PCT Pub. Date: Mar. 31, 1994

[30] Foreign Application Priority Data

Sep. 19, 1992 [GB] United Kingdom .................... 9219849

[51] Int. Cl.⁶ .................................................. A61M 5/00
[52] U.S. Cl. ................... 604/207; 604/209; 604/224; 222/391
[58] Field of Search ................... 604/207–211, 218, 604/224, 135, 186; 222/46, 309, 390, 391

[56] References Cited

U.S. PATENT DOCUMENTS

| 4,592,745 | 6/1986 | Rex et al. ........................ 604/211 |
| 4,641,766 | 2/1987 | Vlasich ........................... 222/391 |
| 4,973,318 | 11/1990 | Holm et al. ...................... 604/208 |
| 5,226,895 | 7/1993 | Harris ............................ 604/208 |
| 5,226,896 | 7/1993 | Harris ............................ 604/211 |
| 5,279,585 | 1/1994 | Balkwill ......................... 604/207 |
| 5,433,352 | 7/1995 | Ronvig ........................... 222/391 |
| 5,478,316 | 12/1995 | Bitdinger et al. ................. 604/135 |

FOREIGN PATENT DOCUMENTS

| 3840000 | 7/1989 | Denmark . |
| 0295075 | 12/1988 | European Pat. Off. . |
| 1230522 | 5/1971 | United Kingdom . |

*Primary Examiner*—Corrine M. McDermott
*Assistant Examiner*—Cris L. Rodriquez
*Attorney, Agent, or Firm*—Charles D. Gunter, Jr.

[57] ABSTRACT

The present invention relates to a syringe for delivering only a single dose of a medicament at each actuation of the syringe. The device includes a cylinder which is adapted to contain the medicament, the cylinder having a piston which is journalled in the bore of the cylinder for axial movement in the bore towards an outlet. The piston can be moved axially within the bore of the cylinder by means of a plunger member which carries one or more drive teeth which are adapted to engage teeth carried by an axially moveable drive member. The axial spacing between the axially adjacent teeth on either the plunger member or the drive member corresponds to the forward axial movement of the plunger member which is required to discharge a single dose of medicament. The drive member can also be retracted axially only a predetermined distance which corresponds to one of the tooth spacings with respect to the plunger.

5 Claims, 3 Drawing Sheets

SYRINGE WITH INCREMENTALLY ACTUATED PLUNGER

The present invention relates to a device, notably to a single dose syringe.

BACKGROUND TO THE INVENTION

Medicaments are often administered to a patient by means of a syringe in which the user depresses the exposed end of a plunger journalled axially in the syringe body to drive a piston journalled within the bore of the syringe body a given axial distance to eject a quantity of fluid from the syringe body through a needle mounted at the distal end of the syringe body, ie. that end removed from the end at which the user acts upon the exposed end of the plunger shaft. The amount of fluid ejected will depend upon the extent of movement of the plunger and this is typically assessed by the user monitoring a number of clicks or other audible signals generated as the plunger is moved. Alternatively, the user can monitor the extent movement against a fixed scale or the like.

Where a single dose is to be administered, the user often draws sufficient fluid into the barrel of the syringe from a bottle or the like by retracting the plunger to draw fluid into the body of the syringe through the needle and ejects the whole of that dose by a single depression of the plunger. However, this is inconvenient where repeated doses of the same medicament are to be administered. It is therefore customary for a syringe to incorporate a cartridge or other reservoir so that a user can administer a number of dosages without the need to replace the source of the medicament after each dosage. The syringe mechanism is therefore designed to permit repeated actuation of the plunger and means must be provided for enabling the plunger to be moved the desired amount for each dose and, usually, for the user to select the dosage to be administered. However, this carries the risk that the user may administer an over or under dose by incorrect selection of the amount of medicament discharged from the cartridge or reservoir, and/or by repeated partial actuation of the device, for example where the user has a tremulous hand.

Various forms of dosage selection mechanism have been proposed, see for example European Patent Application No 0037696 A1 and British Patent Application No 2109690 A. However, such mechanisms rely upon the accurate selection of the dosage by the user and accurate operation of the device if consistent dosages are to be achieved.

It has been proposed in, for example British Specification No 1230522, to form a number of tangentially and axially off set radial projections on the shaft of the plunger, the axial off set of each of which corresponds to the axial movement of the plunger required to administer a selected dose. The proximal end of the syringe body carries a transverse plate through which the plunger shaft passes. The plunger can be moved axially until the distal end of one of the projections engages the face of the transverse plate and thus halts further axial movement of the plunger. The plunger must then be rotated about its longitudinal axis to bring the projection into alignment with a radial slot in the plate which allows the projection to pass axially through the plate and thus allow further movement of the plunger until the next projection engages the face of the plate. Such a device provides means for discharging single doses from the syringe, However, the user can administer partial doses by incomplete depression of the plunger and can retract the plunger during use, for example by operating the plunger tremulously, to administer an unknown dose of medicament.

It has been proposed in European Patent Application No 0225439 A1 to provide the plunger of a syringe with an axial series of radially projecting teeth on each side thereof and to pass the plunger shaft through a transversely moveable block member which carries a second series of teeth adapted to engage with the teeth on the plunger. The block member is urged radially by a spring so that the teeth on the block engage those on the plunger and thus prevent axial movement of the plunger. When the block member is depressed against the spring, the engagement between the teeth is broken to allow the plunger to move axially. In order to limit the forward movement of the plunger, there is provided a spring loaded arm pivoting about a transverse axis, the arm carrying a third set of axial teeth which partially engages with the teeth on the top face of the plunger. By virtue of the arc of swing of the arm, the teeth it carries progressively engage with the teeth on the plunger as the plunger moves axially forward, until the teeth are fully engaged and prevent further axial travel of the plunger.

Such a mechanism is said to restrict forward movement of the plunger to a series of pre-set incremental movements. However, the mechanism requires concerted movement of the block and arm members to alternately secure and release the plunger. Furthermore, the plunger can be withdrawn an indeterminate distance when the teeth of the block member are disengaged from the teeth on the plunger. A user therefore does not know how much potential forward movement of the plunger is available in the device and hence the dosage which will be administered.

We have devised a form of syringe operative mechanism which reduces the above problems.

SUMMARY OF THE INVENTION

Accordingly, the present invention provides a device for the administration of a medicament by means of a needle adapted to be inserted into the body of a person, which device comprises a cylinder adapted to contain the medicament and having a piston journalled in the bore of the cylinder for axial movement in the bore towards an outlet provided with the needle or adapted to receive the needle in mounting engagement therewith, the piston being adapted to be moved axially within the bore of the cylinder by means of a plunger member, which plunger member carries one or more drive teeth adapted to engage with teeth carried by an axially moveable drive member adapted to be acted upon by the user, characterised in that:

a. the axial spacing between axially adjacent teeth on one of the plunger member or the drive member corresponds to the forward axial movement of the plunger member required to discharge a single dose of the medicament; and b. means are provided for retracting the drive member axially a predetermined distance corresponding to one said tooth spacing with respect to the plunger whereby forward axial movement of the drive member with the teeth of the drive and plunger members engaged is adapted to administer said single dosage of the medicament.

By providing the spacing between the teeth on the plunger or the drive first member at the equivalent of one dosage axial movement and limiting the retraction of the other member with respect to the first member to the axial distance corresponding to a single dose travel, the device can deliver only a single dose of medicament per actuation of the device. The device of the invention thus avoids the need to provide dosage selection means with the attendant risk that the user may select an incorrect dose.

For convenience, the invention will be described hereinafter in terms of the plunger carrying drive teeth which have the required single dose travel spacing and the drive member being the member whose axial extent of retraction is limited to that single dose travel.

Furthermore, due to the spacing of the teeth on the plunger member and the limit on the extent of movement of the drive member, the teeth on the drive member cannot engage the next axial location upon the plunger until the plunger has moved axially for it full extent of travel for the dose being discharged, since the next teeth on the plunger to be engaged by the drive member will not be fully exposed for engagement by the drive member until the plunger has completed its forward stroke. If the drive between the drive member and the plunger member of the device of the invention is inadvertently disengaged before the forward stroke of the plunger has been completed, the teeth of the drive member and the plunger will be out of register at all permitted positions of travel of the drive member and will not re-mesh with one another, except at the exact point where disengagement took place. It is necessary to relocate the drive member exactly with respect to the plunger member to enable the teeth on the drive member to mesh with the teeth on the plunger member and thus allow the drive to be re-engaged. Thus, the user can discharge only a complete dose, even where the drive is accidentally disengaged during operation and cannot re-engage the drive at a position which would allow excessive or insufficient medicament to be discharged.

Preferably, means are provided whereby the drive member cannot be disengaged from the plunger member intermediate the extremes of travel of the drive member during the administration of a complete dose and re-engagement of the drive and plunger members can only be achieved at the rearward extreme of the travel of the drive member. The device therefore cannot be operated to deliver anything but a single full dose of the medicament and a user has to complete the delivery stroke before the drive member can be retracted to prepare the device for delivery of a subsequent dose.

Preferably, the drive member is spring or otherwise biassed to its axially fully retracted position at which its teeth can mesh with the teeth of the plunger member at the start position for the forward movement of the plunger member for the administration of each dose of medicament.

Preferably, the engagement and disengagement of the drive member teeth from the drive teeth of the plunger member require a positive action, eg. relative rotation between the drive member and the plunger member, by the user at the forward end of the plunger stroke and the rearward end of the drive member stroke. Such positive disengagement of the drive between the drive and plunger members permits relative axial movement between the plunger member and the drive member whilst the drive member is retracted and the plunger member remains stationary. This substantially prevents inadvertent operation of the device to administer multiple dosages. Preferably, the plunger member is prevented from axial retraction by ratchet or other means acting upon the plunger member whereby the plunger is prevented from being retracted as the drive member is retracted, thus achieving uni-directional drive of the plunger by the drive member.

The device of the invention comprises a body portion which can be of any suitable shape and design and which houses the plunger and drive mechanism. The invention can be applied to syringes in which a plurality of doses of the medicament are held within the bore of the syringe body which forms the cylinder containing the piston against which the plunger member acts and from which the doses of medicament are discharged by progressive movement of the piston axially in the bore. However, the invention is of especial application where the medicament is held in a replaceable cylindrical cartridge attached to the distal end of the syringe body, the cartridge having a piston journalled in the bore of the cartridge.

For convenience, the invention will be described hereinafter in terms of a syringe body carrying a replaceable medicament cartridge at the distal end of the syringe body.

Preferably, the syringe body portion is similar to a conventional syringe body which is adapted to receive a medicament cartridge at the distal end of the body. The cartridge provides the cylinder and piston, the body of the syringe providing an axial housing which carries the drive member and the plunger member which acts directly or through a member operatively associated therewith on the piston in the cartridge. The assembled cartridge and housing thus have a generally cylindrical configuration with radial symmetry about the longitudinal axis of the device. The cartridge can be of any suitable type and many are available commercially and will usually be secured to the syringe body by a bayonet, screw or other fit of the cartridge into a recess at the distal end of the syringe body.

Preferably, the cartridge is secured to the distal end of the syringe body by means of a generally cylindrical holder within which the cartridge is secured, for example the cartridge is a push fit within the holder. Alternatively, the cartridge is secured within the holder by means of snapfit ribs or the like which engage the rim below the crimped end cap usually present in commercially available medicament cartridges. Since the holder can usually be made to closer dimensional tolerances than the glass body of the cartridge, location of the distal end of the cartridge accurately within the holder provides an accurate positioning of the distal end of the cartridge with respect to the travel of the plunger when the holder is mounted on the syringe body. It is also preferred that the holder be secured to the syringe body by means of a screw thread so that minor inaccuracies in the fabrication of the device and the holder can be accommodated.

Preferably, the rearward rim of the cartridge or the holder engages radial lugs or the like carried within the recess in the syringe body into which the cartridge/holder locates. The lugs act to cause ratchet teeth to engage with teeth on the shaft of the plunger so as to prevent rearward movement, ie. retraction, of the plunger once the cartridge/holder has been secured in position. In a particularly preferred embodiment, the lugs take the form of two or more axially extending arms located in the base of the recess and having a tapered radially outward faces. The arms carry the ratchet teeth upon their radially inward faces. As the rim of the cartridge or holder rides axially rearward along the arms as the cartridge/holder is inserted into the recess, it flexes the arms inwardly and brings the ratchet teeth into engagement with the teeth on the plunger member. When the cartridge/holder is mounted fully home upon the syringe body, the ratchet teeth prevent retraction of the plunger so that the plunger remains static when the drive member is retracted between actuations of the device. However, as the cartridge/holder is removed from the syringe body, the ratchet teeth are disengaged from the plunger, for example the arms carrying the ratchet teeth are allowed to flex outwardly and to carry the ratchet teeth clear of the teeth on the plunger. When the ratchet teeth are disengaged from the plunger and the cartridge/holder removed to expose the distal end of the plunger, the plunger can be extended to engage the piston within a replacement cartridge/holder as it is offered up to the body of the syringe. The plunger is then free to retract as the cartridge/holder is secured to the syringe until the ratchet teeth are engaged with the plunger as the cartridge/holder rim seats home in the recess. The distal end of the plunger is thus located against the piston and it is not necessary for a user to operate the device several times to advance the plunger into engagement with the piston when the device is first used.

The teeth on the shaft of the plunger which engage the ratchet teeth are preferably a separate set of teeth from those, the drive teeth, which are to engage the teeth on the drive member, and are located adjacent the distal end of the plunger shaft. Preferably, this separate set of teeth have a finer axial spacing than the drive teeth on the plunger, so that engagement of the ratchet teeth with the separate teeth can occur over smaller axial intervals of the movement of the plunger. In order that the engagement of the various sets of teeth can be synchronised, the separate teeth have an axial spacing which is an integer sub-multiple of the axial spacing of the drive teeth on the plunger, typically one third or a quarter.

The syringe body contains the plunger/drive mechanism which is used to advance the piston in the cartridge. Typically, the plunger and drive members are orientated upon the longitudinal axis of the syringe body and the drive member is provided with one or more teeth which are directed radially inwardly to engage the drive teeth on the plunger which are directed radially outward. However, the device may be configured with the teeth on the drive member directed outwardly to act on inwardly directed drive teeth carried by a sleeve acting as the plunger or a connection between the plunger and the drive members. For convenience, the invention will be described hereinafter in terms of a substantially solid plunger member carrying radially outwardly directed drive teeth which engage with radially inwardly directed teeth carried by the drive member, at least the distal end of which is in the form of a sleeve within which the plunger is journalled or in the form of a separate sleeve member forming the distal end of the drive member and operatively connected to the remainder of drive member.

In the device of the present invention, the teeth on each of the drive and plunger members can be the same or different but are of forms which can mutually engage so as to provide a positive drive between the drive member and the plunger on the forward stroke of the drive member. However, it is preferred that the tooth on the drive and plunger members be of the same form so as to facilitate engagement and disengagement of the teeth. The teeth are preferably of a squared cross-section. However, they can have a ratchet or a saw tooth configuration so that the drive teeth on the plunger member present a rearwardly facing scarp face, typically at substantially 90° to the longitudinal axis of the plunger member, with a forward inclined face which extends to the foot of the scarp face of the preceding tooth. However, the slope need not extend fully to the foot of the preceding tooth, but there may be an axially flat portion between successive teeth. The teeth on the drive member are similar but of the reversed configuration so that the rearward or scarp face of a plunger drive tooth is engaged by the forward or scarp face of a drive member tooth. If desired, the opposed faces can be inclined so that they lockingly engage.

The axial pitch or spacing between the teeth is such that the plunger is driven forward axially by the drive member one plunger drive tooth space for each actuation of the device and this distance of travel corresponds to that required at the piston to discharge a single dose of medicament from the cartridge. Preferably, the plunger member carries an axial series of drive teeth spaced apart by the travel required for a single dose and the drive member carries one tooth to engage the drive teeth successively.

As stated above the axial retraction of the drive member is limited to the axial spacing between adjacent drive teeth on the plunger member. Preferably, the drive member travels between axially spaced apart stop members so that its axial travel is limited in each direction and registration with the teeth of the plunger member at the rearward extend of its travel is facilitated. Preferably, the drive member is spring loaded to the axially rearward stop. In this way, once the drive member has completed its forward stroke and engages the forward stop member, the drive mechanism can be disengaged and the drive member automatically retracts to the axially rearward stop at which the tooth/teeth of the drive member will register with the next gap(s) between the drive teeth on the plunger member so that the drive can be re-engaged for the subsequent dose.

The plunger and drive members are formed so that the drive member can be moved axially rearwardly with respect to the plunger member. As indicated above, it is preferred that the plunger member be journalled in an axial bore within the drive member and that the teeth of the drive member are carried at the distal end of the bore or of a separate sleeve member which forms the distal end of the drive member. Thus, the teeth of the drive member can be sprung, for example by splitting the side wall of the sleeve member or distal end of the drive member to form axial spring arms carrying the teeth, so that they ride over the drive teeth of the plunger member when the drive member is retracted axially but re-engage automatically when the drive member moves forward with respect to the plunger to provide a uni-directional drive between the drive and plunger members.

However, it is preferred to form the plunger and/or the drive member so that some positive action by the user is required to disengage and re-engage the drive between the two members. Thus, the plunger can be formed with two opposed flatted faces, and the drive member carries its teeth along two diametrically opposed axial lines. Upon rotation of the plunger and drive members through 90° with respect to one another about their longitudinal axes, the teeth on the drive member are brought into register with the flatted faces of the plunger and therefore no longer engage the drive teeth on the plunger member. Rotation through a further 90° or, preferably, rotation back through 90° re-engages the teeth on the drive and plunger members to re-establish the positive drive between the plunger and drive members. If desired, stops or other means can be provided to limit the extent and direction of relative rotation of the drive and plunger members.

Relative rotation of the plunger and drive members can be achieved by providing the drive member with a radially protruding pin or the like which engages in a guide slot or track in a portion of the syringe body within which the drive member is journalled, which portion can be rotated relative to the remainder of the syringe body to bring the teeth on the drive member out of and into engagement with the drive teeth on the plunger member at the forward and rearward extremities respectively of the axial travel of the drive member. Alternatively, the drive member, or a member operatively associated therewith, can extend rearwardly beyond the proximal limit of the syringe body to provide an exposed end cap which can be used both to move the drive member axially and to rotate the drive member.

Alternatively, the distal end of the drive member can be provided with two or more axial arm members which carry the teeth to engage the drive teeth of the plunger member. The arm members can be carried by a separate connecting member or sleeve which operatively connects the remainder of the drive member and the plunger member. The arm members are adapted to flex or pivot radially so that the teeth carried by the arms can be brought into and out of engagement with the drive teeth on the plunger member by radial movement of the arms relative to the plunger member. Preferably, the arms are moved radially by a suitable cam mechanism carried internally by a rotatable sleeve member of the syringe body so that the teeth on the arms are brought radially into engagement with the drive teeth of the plunger member to engage the drive, but are allowed to splay when the drive is to be disengaged from the plunger. Suitable forms of such a radially acting clutch mechanism are described and claimed in our European Patent No 0037696 and our European Patent Application No 0295075 A. Other forms of disengageable drive or clutch mechanism may be used if desired.

The plunger member is also preferably provided with means, for example a pawl mechanism or a Torridon drive mechanism, which engages the teeth on the plunger member or the shaft of the plunger member so to prevent axial retraction of the plunger as the drive member is retracted. As stated above, such a mechanism can be interlinked with the mounting of a medicament cartridge/holder upon the distal end of the syringe body so that it is engaged when the cartridge/holder is mounted upon the syringe body, but can be disengaged when the cartridge/ holder is removed so as to allow the plunger member to be at least partially retracted into the syringe body to permit a new cartridge/holder to be fitted.

As stated above, the drive member is preferably biassed to retract to a rearward stop and travels on its forward stroke to engage a forward stop, so as to define the extent of its travel. It is preferred also to provide the rearward end of the plunger member with a radial stop member. For example, the proximal end of the plunger can be formed as a full diameter component rather than with opposed flatted faces, to provide an annular shoulder which advances as the plunger advances. This stop will eventually engage the drive member, for example the rearward faces of the teeth carried by the drive member. Thus, when the plunger member has travelled for the total of all its possible forward travel and all doses within the cartridge have been dispensed, the drive member is trapped between the stop at the proximal, ie. rearward, end of the plunger and the forward stop defining the forward extent of travel of the drive member so that the drive member is prevented from advance or retraction. The user is thus given a positive indication as to when the device cannot deliver more medicament and a new cartridge/holder is required.

The relative dimensions of the components of the device of the invention can be varied over wide ranges to suit the volume of the dosage to be discharged and the size of the cartridge housing to be used; and the device can readily be made from plastic or other materials using known techniques.

DESCRIPTION OF THE DRAWINGS:

To aid understanding of the invention, it will now be described by way of illustration only with respect to the accompanying drawings in which.

DESCRIPTION OF THE PREFERRED EMBODIMENT

Figure 1:
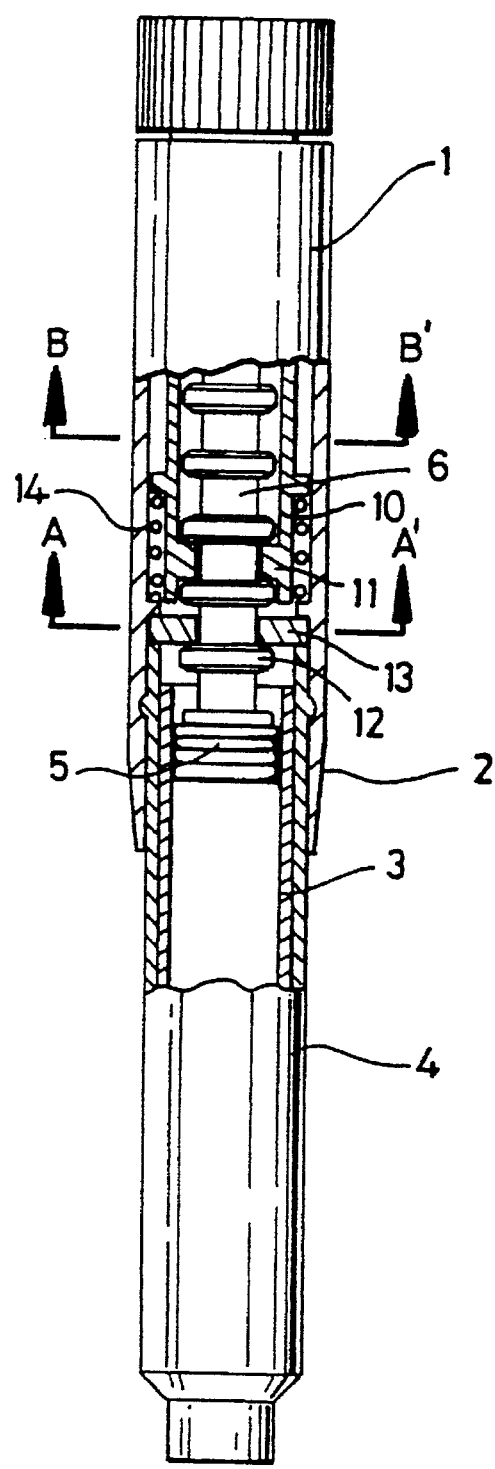
FIG. 1 is an axial sectional view through a device of the invention.

A syringe of the invention comprises a cylindrical housing 1 having a distal end 2 into which a cartridge 3 can be mounted by means of a cartridge holder 4 which is a snap or screw fit into the distal end of the housing 1. Within the cartridge is journalled a piston 5 which is moved incrementally axially by a plunger 6. Plunger 6 can be part of the syringe body, with the piston 5 being part of the replaceable cartridge, or the piston 5 can be carried by the plunger 6 as an integral part of the syringe body.

The distal end of the cartridge holder 4 and/or the cartridge 3 carry a capillary needle, not shown, for injecting medicament into the body of a user.

Within body 1 is journalled an axially moveable drive sleeve member 10 carrying a radially inwardly projecting shoulder which forms a single circumferential tooth 11 which engages with radially outwardly projecting drive teeth 12 carried by the plunger 6. The teeth can have the squared profile as shown in FIG. 1, or can have a saw tooth or other configuration which achieves a positive drive between the plunger 6 and the sleeve 10. The axial spacing between successive drive teeth 12 corresponds to the axial movement of plunger 6, and hence of piston 5, required to discharge a single dose of the medicament from the cartridge 3.

The forward end of sleeve 10 butts against an annular shoulder 13 formed at the forward extreme of the travel of sleeve 10 so as to define the limit of travel for the sleeve. A similar stop, not shown, defines the limit of the rearward travel, or retraction, of the sleeve 10. A spring 14 is trapped between sleeve 10 and stop 13 or their equivalents so that sleeve 10 is biassed towards its fully retracted position. The axial spacing between the forward and rearward stops is such that the tooth 11 on sleeve 10 moves axially for the distance required to discharge a single dose of medicament from the cartridge 3 so that when the tooth 11 engages a tooth 12 it will move the plunger 6 axially for this distance. When the sleeve 10 buts against the forward stop 13, it can be disengaged from the drive tooth 12 as described below and sleeve 10 allowed to retract to engage the rearward stop. At this point, the axially forward face of tooth 11 will register with the axially rearward face of the next drive tooth 12 so that the drive between the drive member 10 and the plunger 6 can be reengaged. If the sleeve 10 has not been fully retracted, it will be appreciated that the teeth 11 and 12 will foul one another and the drive cannot be re-engaged.

Figure 2:
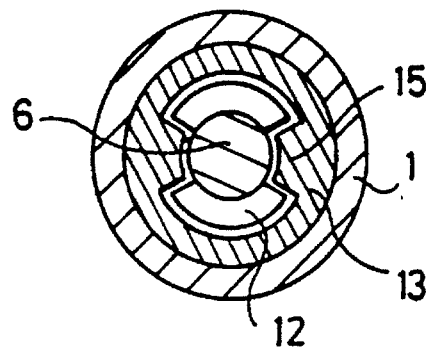
FIGS. 2 and 3 are transverse cross-sectional views through the device of FIG. 1 along the lines A–A' and B–B' respectively.
Figure 3:
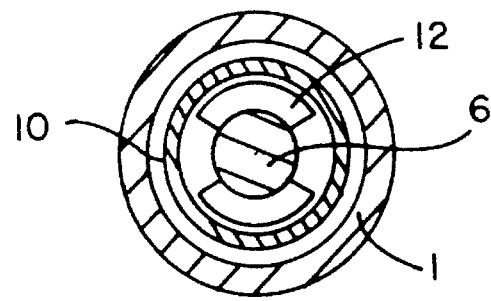

The drive teeth 12 carried by the plunger 6 have an interrupted arcuate shape as shown in FIGS. 2 and 3 which marries with radially inward projections 15 in the plan shape of the annular shoulder 13. As shown in FIG. 2, the plunger and its teeth 12 are orientated so that the interruptions in the drive teeth correspond to the inward projections 15 of the shoulder 13 so that the plunger can move freely past shoulder 13, whereas the forward end of sleeve 10 cannot pass projections 15 which thus act as a forward stop to the travel of sleeve 10.

Figure 4:
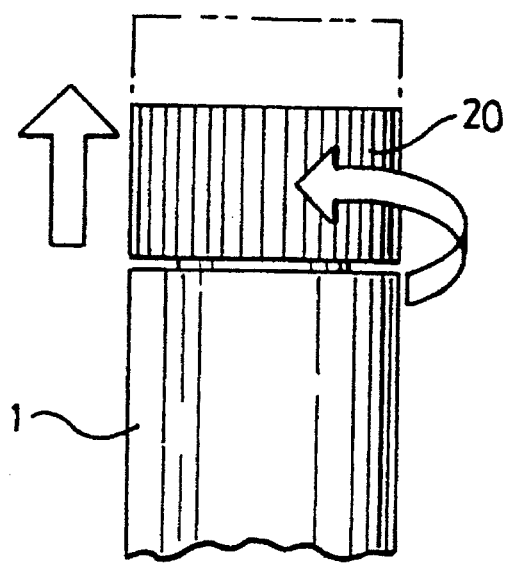
FIGS. 4 and 5 are views of the top end of the device in two states of operation.
Figure 5:
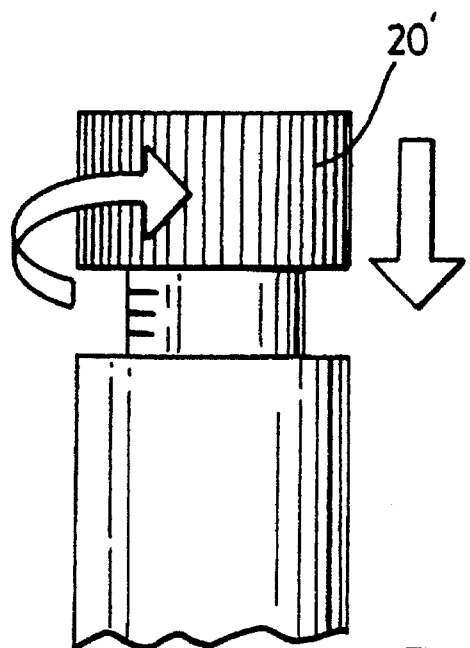
Figure 6:
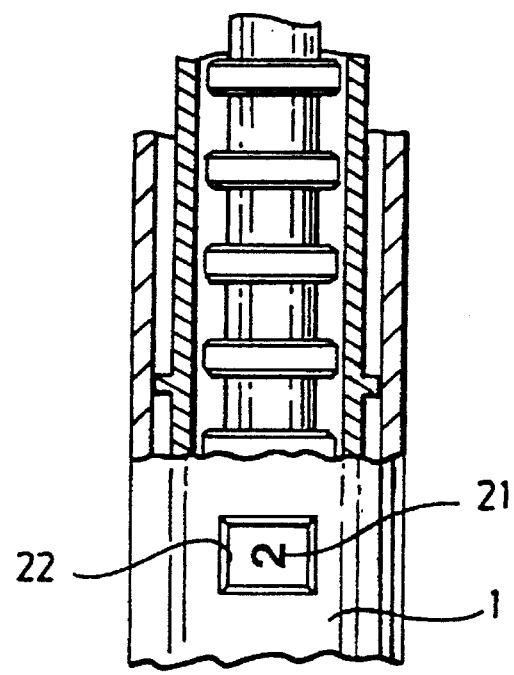
FIG. 6 shows an alternative form of the device.

Sleeve 10 extends rearwardly to a knurled push button end 20 projecting from the end of the housing 1. The teeth carried internally upon sleeve 10 are circumferentially interrupted in the same manner as shoulder 13 so that they engage the drive teeth 12 on plunger 6 in one angular orientation but do not engage when sleeve 10 is rotated about its longitudinal axis, so as to provide a hit or miss type of clutch between the sleeve 10 and plunger 6. Thus, when button end 20 is rotated to bring the teeth 11 into register with the teeth 12 on plunger 6 the drive between member 10 and plunger 6 is engaged and axial forward movement of member 10 will advance plunger 6. However, when end 20 is rotated through 90° the teeth 11 are carried out of register with the teeth 12 and the drive is disengaged. Sleeve 10 can then be retracted under the bias of spring 14 until sleeve 10 (carrying the end 20) butts against its rearward travel limiting stop, as shown dotted in FIG. 4. The sleeve 10 has moved axially one drive tooth spacing with respect to the plunger 6 and contra-rotation of button end 20 brings the teeth 11 on the sleeve into register with the teeth 12 on the plunger so as to re-engage the drive between the sleeve and the plunger. Button 20 can now be depressed as shown in FIG. 5 to return sleeve 10 forwardly to butt against stop 13. This drives piston 5 one dose axially along the bore of the cylinder of cartridge 3. As shown in FIG. 6, the plunger 6 can carry numbers or other markings 21 to register with a window or clear portion 22 of housing 1 to display the number of doses administered or remaining to be administered from the cartridge 3.

It will be appreciated that the plunger and member 10 can carry more that two diametrically opposed sets of teeth as shown, for example the teeth could be arranged as three axial rows of teeth on each of the plunger and drive member at 120° spacings rather than 180° spacings.

When the drive member has been moved to its axially forward extreme of travel, the device will be in the position shown in FIG. 1 and can not administer another dose until sleeve 10 has been disengaged from plunger 6, retracted to its full extent and the drive with plunger 6 re-engaged as described above.

Preferably, the device is provided with means whereby the drive between the sleeve 10 and plunger 6 cannot be disengaged during the forward travel of the sleeve and plunger. Thus, for example, the sleeve 10 carries a radially protruding pin which engages in an axial groove or guide in the wall of the housing, which has a 90° circumferential cross portion at each end The sleeve, plunger, pin and guide are configured so that the teeth carried by the sleeve engage with the drive teeth carried by the plunger when the sleeve is aligned with the pin in the axial portion of the guide, but are disengaged when the pin is at the extreme of the circumferential cross portions of the guide. When the pin is carried out of engagement with the cross portion of the guide as the relative rotation of the sleeve and plunger is completed at the forward extreme of travel of the sleeve, the sleeve is released from the guide and can retract freely under the influence of the spring to align the pin axially with the entry to the axially rearward cross portion of the guide. In this way the positive drive between the sleeve and plunger can only be engaged or disengaged at either end of the full travel of the pin in the axial slot, the sleeve can retract with respect to the plunger only when the drive is disengaged at the forward extreme of travel of the sleeve, and the drive re-engaged only at the rearward extreme of travel of the sleeve.

Figure 7:
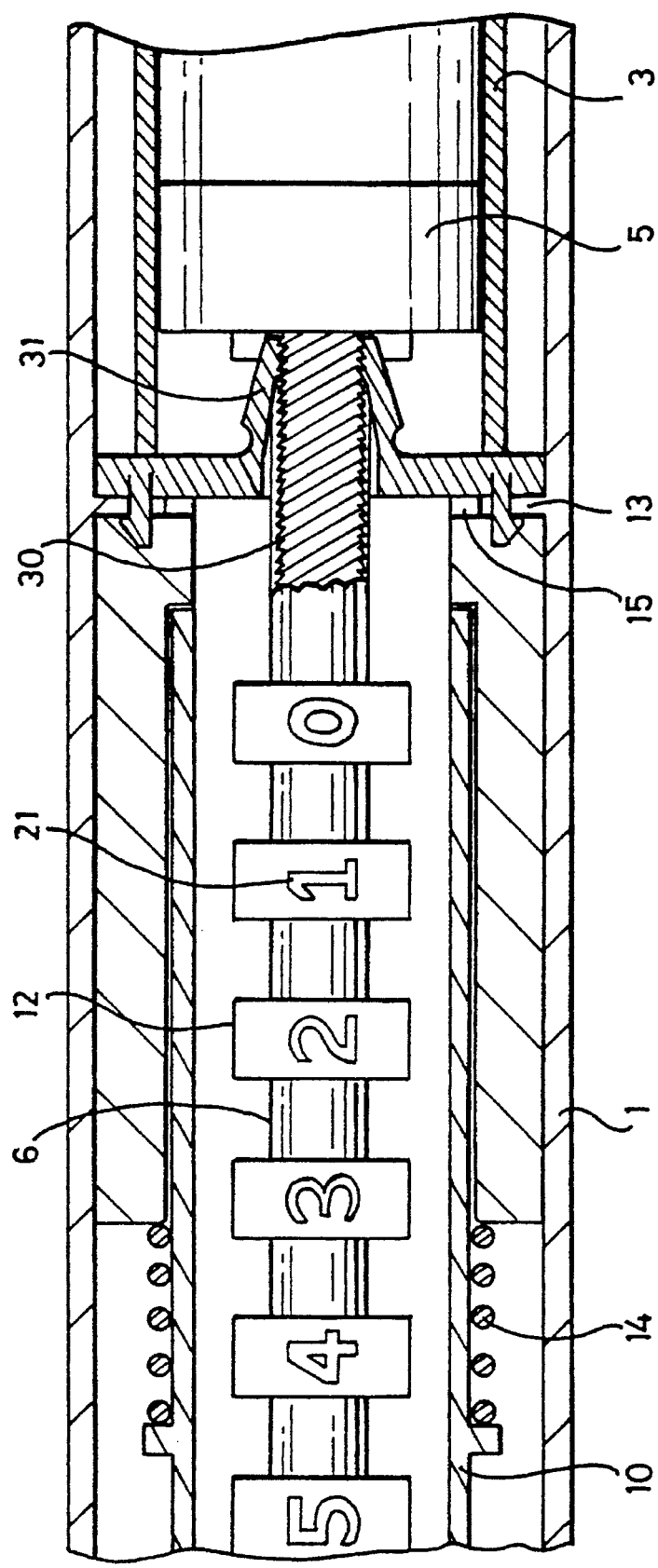
FIG. 7 shows a form of the device incorporating a non-retraction ratchet for the plunger.

Preferably, the plunger 6 is provided with means which prevent axial retraction of the plunger when the sleeve 10 is retracted. As described above this can be achieved by providing disengagable ratchet teeth at the distal end of the syringe body which are actuated by the mounting of the cartridge/holder upon the syringe body and which engage with the drive teeth 12 on the plunger. However, such teeth 12 are usually comparatively widely spaced axially and it is preferred, as shown in FIG. 7, that the plunger can carry a secondary set of finer pitched teeth 30 which engage with a non-retraction ratchet mechanism 31 so that plunger 6 can not be retracted when sleeve 10 is retracted, thus preserving the one dose relative axial movement requirement before the drive can be re-engaged.

The invention has been described above in terms of the sleeve 10 and the plunger 6 carrying teeth where the teeth have a single dose spacing. However, it is within the scope of the present invention to utilise more than one set of teeth on either or both of the sleeve and plunger, provided that the effect of the intermeshing of those sets of teeth is to ensure that the plunger moves only one dose distance axially upon each actuation of the device and that the drive between the sleeve and plunger cannot readily be disengaged and re-engaged except at each end of the axially travel of the sleeve. It will also be appreciated that the sleeve and plunger can be interchanged so that the button end 20 acts upon the plunger which then acts upon the sleeve which engages the piston 5; and that the plunger member can carry a single tooth which is engaged by successive teeth carried by the drive member which are spaced apart by the single dose travel distance. If desired, the drive member 10 can be spring or otherwise biassed to the forward end of its travel and the proximal end of the syringe housing can be provided with a suitable cam or other profile against which the end cap 20 bears so that rotation of the end cap initially disengages the drive between the drive member and the plunger, further rotation causes the end cap and hence the drive member to which it is linked to be moved axially rearwardly for the retracttion of the drive member with respect to the plunger member, further rotation re-engages the drive between the drive member and the plunger, and then releases the end cap for forward axial movement under the bias of the spring or other means to drive the plunger member forward and discharge the-dose of medicament.

What is claimed is:

1. A device for the administration of a medicament by means of a needle adapted to be inserted into the body of a person, which device comprises a cylinder (3) adapted to contain the medicament the cylinder having a bore and having a piston (5) journalled in the bore of the cylinder for axial movement in the bore towards an outlet provided with the needle or adapted to receive the needle in mounting engagement therewith, a plunger member for moving the piston (5) axially and incrementally within the bore of the cylinder (3) the plunger member (6) carrying one or more radially projecting teeth (12), an axially extending drive member (10) carrying one or more drive teeth (11) adapted to engage with the teeth (12) carried by the plunger member (6) and to move the plunger (6) axially for that distance required to discharge a single dosage of the medicament upon each actuation of the drive member (10) by a user, wherein:

a. the axial spacing between axially adjacent teeth (12 or 11) on one of the plunger member (6) or the drive member (10) corresponds to the forward axial movement of the plunger member (6) required to discharge a single dose of the medicament;

b. forward stop members (13) are provided which define the limits of the forward axial movement of the drive member (10) to a predetermined distance corresponding to one said tooth spacing with respect to the plunger (6), whereby forward axial movement of the drive member (10) with the teeth (11) and 12) of the drive and plunger members (10 and 6) engaged is adapted to administer said single dosage of the medicament;

c. biasing means located within the cylinder and contacting the drive member (10) for biasing the drive member (10) to its axially fully retracted position at which its drive teeth (11) is/are brought into meshing register with the teeth (12) of the plunger member (6) at the start position of the forward movement of the plunger member (6);

d. the drive member (10) and the plunger member (6) are mounted within the cylinder for rotation relative to one another about their longitudinal axes to bring the teeth (11 and 12) of the drive and plunger members (10 and 6) into and out of meshing engagement with each other and means are provided for preventing such relative rotation intermediate the rearward and forward extremes of travel of the drive member (10).

2. A device as claimed in claim 1, wherein ratchet means (30, 31) are provided on the plunger member whereby the plunger member (6) is prevented from axial retraction whilst the drive member (10) is being retracted.

3. A device as claimed in claim 1, wherein the plunger member has a series of successive teeth provided thereon, and wherein the successive teeth (12) on the plunger member (6) are spaced apart axially by the travel required to administer said single medicament dose and the drive member (10) carries only one tooth (11), or vice versa.

4. A device as claimed in claim 1, wherein the teeth (11 and 12) of the drive member and the plunger member have a squared cross-section.

5. A device as claimed in claim 1, wherein the plunger member (6) has flatted axial faces and wherein the drive member (10) has drive teeth (11) carried by the drive member (10) which is/are aligned axially upon the drive member (10) whereby they are adapted to be brought into register with those flatted axial faces to disengage the drive between the drive member (10) and the plunger member (6).

* * * * *